US00PP25847P2

(12) United States Plant Patent
Zary

(10) Patent No.: US PP25,847 P2
(45) Date of Patent: Sep. 1, 2015

(54) MINIATURE ROSE PLANT NAMED 'ZARSUNFRAPK'

(50) Latin Name: *Rosa×hybrida*
Varietal Denomination: ZARsunfrapk

(71) Applicant: American Daylily and Perennials, Inc., Grain Valley, MO (US)

(72) Inventor: Keith W. Zary, Troy, OH (US)

(73) Assignee: American Daylily and Perennials, Inc., Grain Valley, MO (US)

( * ) Notice: Subject to any disclaimer, the term of this patent is extended or adjusted under 35 U.S.C. 154(b) by 0 days.

(21) Appl. No.: 14/545,447

(22) Filed: May 5, 2015

Related U.S. Application Data

(60) Provisional application No. 61/998,872, filed on Jul. 10, 2014.

(51) Int. Cl.
*A01H 5/02* (2006.01)

(52) U.S. Cl.
USPC ..... Plt./121

(58) Field of Classification Search
USPC ..... Plt./121, 128, 148
See application file for complete search history.

*Primary Examiner* — June Hwu

(74) *Attorney, Agent, or Firm* — Barbara Campbell; Cochran Freund & Young LLC

(57) ABSTRACT

A new rose plant designated 'ZARsunfrapk' particularly distinguished by being a landscape (miniature) shrub rose having fragrant pink flowers, a compact growth habit requiring little pruning, easy to root and propagate, shows resistance to powdery mildew, rust, and black spot, grows vigorously on its own roots, shown to be heat tolerant and cold hardy in trials, and hardy to USDA Zones 5 to 10 is disclosed.

2 Drawing Sheets

Genus and species: *Rosa×hybrida.*
Variety denomination: 'ZARsunfrapk'.

BACKGROUND OF THE NEW VARIETY

The present invention comprises a new and distinct variety of rose, botanically known as *Rosa×hybrida*, and hereinafter referred to by the variety name 'ZARsunfrapk'. 'ZARsunfrapk' originated from a cross conducted in June 2009 in Somis, Calif. between the female rose variety 'MORsegold', also commercially known as 'Sequoia Gold' (U.S. Plant Pat. No. 6,617), and the male rose variety KNOCK OUT 'RADrazz' (U.S. Plant Pat. No. 11,836).

The seeds from the cross were sown and plants were grown for evaluation. An individual plant designated 'ZARsunfrapk' was selected in July 2010 in Somis, Calif. 'ZARsunfrapk' was first vegetatively propagated in July 2011 in Tipp City, Ohio by softwood cuttings rooted under mist. 'ZARsunfrapk' was found to reproduce true to type in successive generations of asexual propagation via softwood cuttings, hardwood cuttings, and by budding onto rootstock.

SUMMARY

The following are the most outstanding and distinguishing characteristics of this new variety when grown under normal horticultural practices in Somis, Calif., Tipp City, Ohio, Sarasota, Fla., and Grain Valley, Mo.

1. A landscape (miniature) shrub rose having fragrant pink flowers;
2. A compact growth habit requiring little pruning;
3. Easy to root and propagate;
4. Shows resistance to powdery mildew, rust, and black spot;

5. Flowers produce a good color display for an extended period;
6. Grows vigorously on its own roots; and
7. Shown to be heat tolerant and cold hardy in trials, and hardy to USDA Zones 5 to 10.

DESCRIPTION OF THE PHOTOGRAPHS

This new rose plant is illustrated by the accompanying photographs which show the plants' foliage, buds, and flowers. The colors shown are as true as can be reasonably obtained by conventional photographic procedures. The photos of the plants in FIGS. 1 to 2 were taken outdoors in Grain Valley, Mo. in June 2013, and the plants were 2-years-old. The photo of the plant parts in FIG. 3 was taken in Tipp City, Ohio, in September 2014 from a two-year-old plant.

Figure 1:
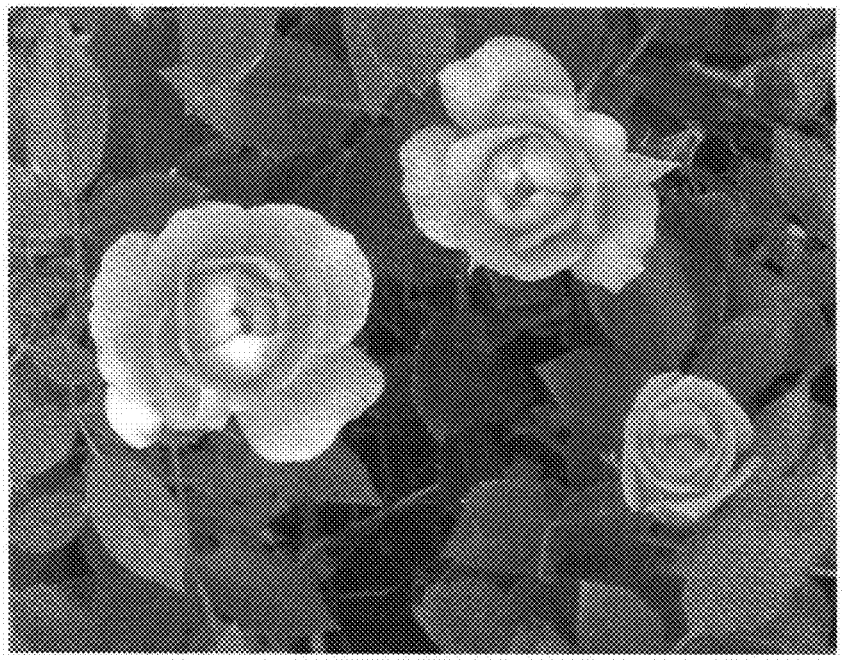
FIG. 1 shows the foliage and flowers opening of 'ZARsunfrapk'.
Figure 2:
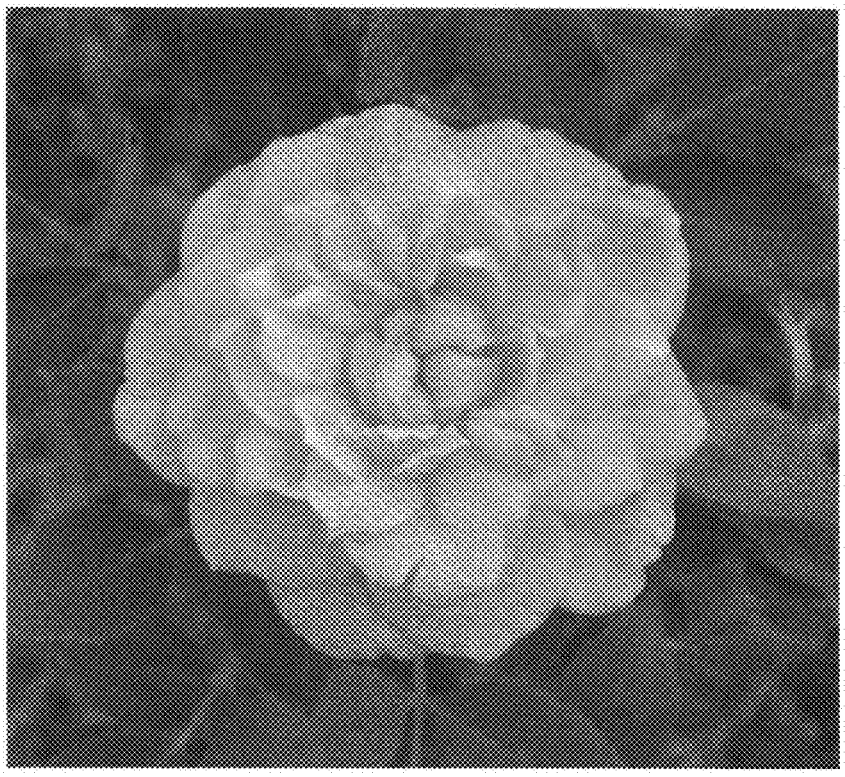
FIG. 2 shows a close-up the flower of 'ZARsunfrapk'.
Figure 3:
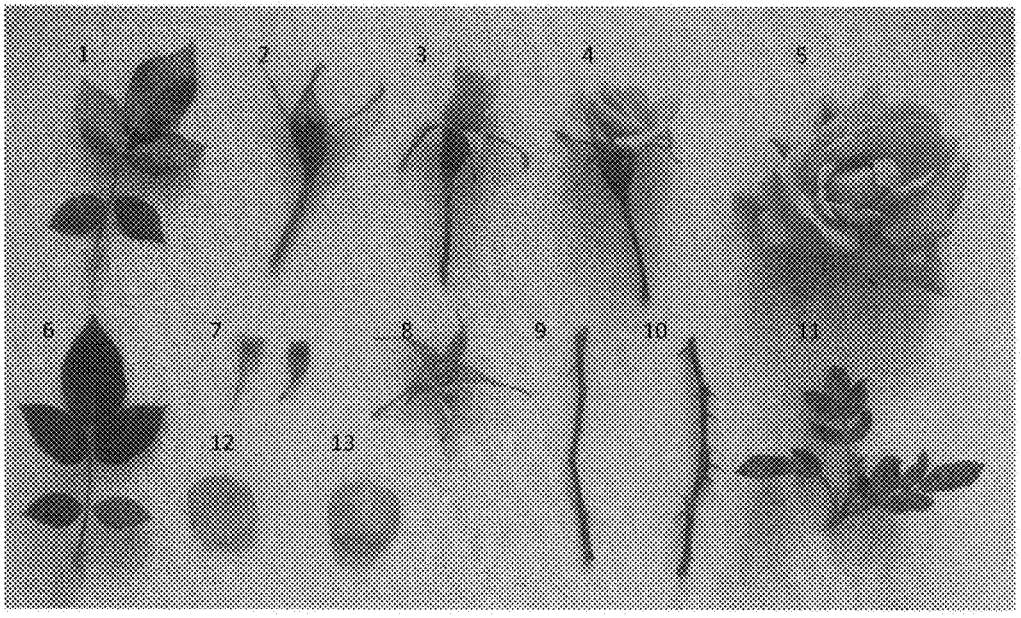
FIG. 3 shows a close-up of individual flower parts of the plant of 'ZARsunfrapk', where.

1 shows the lower surface of a mature leaf and the leaflets
2 shows a closed flower bud
3 shows the flower as it is beginning to open
4 shows the flower as it is opening more
5 shows a fully opened flower
6 shows the upper surface of a mature leaf and the leaflets
7 shows from left to right, the upper and lower surface of the individual sepals
8 shows the upper surface of the calyx with the petals removed
9 shows a section of an immature stem with thorns
10 shows a section of a mature stem with thorns
11 shows three immature leaves and their leaflets attached to a stem

12 shows the upper surface of a petal
13 shows the lower surface of a petal

DESCRIPTION OF THE NEW VARIETY

The following detailed descriptions set forth the distinctive characteristics of 'ZARsunfrapk'. The data which define these characteristics were collected from asexual reproductions carried out in Tipp City, Ohio between July to October 2014. Data was collected on 2-year-plants, growing on their own roots, outdoors. The plants were not sprayed and were fertilized at a rate of 100 ppm of Nitrogen, Phosphorous, and Potassium. Color references are to The R.H.S. Colour Chart of The Royal Horticultural Society of London (R.H.S.), (2001).

Classification:
- *Family*.—Rosaceae.
- *Botanical*.—*Rosa×hybrida*.
- *Designation*.—'ZARsunfrapk'.

Parentage:
- *Female parent*.—The female rose variety 'MORsegold', also commercially known as 'Sequoia Gold' (U.S. Plant Pat. No. 6,617).
- *Male parent*.—The male rose variety KNOCK OUT 'RADrazz' (U.S. Plant Pat. No. 11,836).

Plant:
- *Habit*.—Upright, compact, and rounded.
- *Height*.—25.0 cm.
- *Spread*.—20.0 cm.
- *Life cycle*.—Perennial.
- *Time to produce a rooted cutting*.—3 weeks.
- *Root description*.—Fibrous.
- *Time to bloom from propagation*.—8 to 10 weeks.
- *Lastingness of inflorescence on the plant*.—5 to 7 days.

Lateral branches/peduncles:
- *Color*.—RHS 137A (Green).
- *Pubescence*.—Absent.
- *Stem shape*.—Rounded and ascending.
- *Diameter*.—0.2 cm to 0.3 cm.
- *Length*.—10.0 cm to 12.0 cm.
- *Anthocyanin*.—Absent.
- *Thorns*.—Density: 1 per centimeter. Shape: Slightly curved downward. Color: RHS 200D (Brown). Length: 0.5 cm. Width: 0.1 cm at the base.

Foliage:
- *Arrangement*.—Odd pinnate.
- *Quantity of leaflets per leaf*.—5.
- *Leaf length*.—6.0 cm to 7.0 cm.
- *Leaf width*.—4.0 cm.
- *Terminal leaflet*.—Length: 2.0 cm. Width: 1.3 cm. Shape: Elliptic. Apex: Acuminate. Base: Rounded. Margin: Simply serrate. Color, immature leaf: Upper surface: RHS 137B (Green). Lower surface: RHS 146B (Yellow-Green). Color, mature leaf: Upper surface: RHS 137C (Green). Lower surface: RHS 136A (Green). Texture: Upper surface: Smooth, coriaceous. Lower surface: Smooth.
- *Lateral leaflet*.—Length: 2.5 cm. Width: 1.2 cm. Shape: Elliptic. Apex: Acuminate. Base: Rounded. Margin: Simply serrate. Color, immature leaf: Upper surface: RHS 137B (Green). Lower surface: RHS 146B (Yellow-Green). Color, mature leaf: Upper surface: RHS 137C (Green). Upper surface: RHS 136A (Green). Texture: Upper surface: Smooth and coriaceous. Lower surface: Smooth.
- *Leaf venation pattern*.—Reticulate.
- *Leaf venation color*.—Upper surface: RHS 137B (Green). Lower surface: RHS 147C (Green).
- *Petioles, leaves*.—Length: 4.0 cm. Diameter: 0.1 cm. Color: RHS 147C (Yellow-Green). Texture: Rough with many prickles and glands. Thorns: 3 on the petiole, hooked downward and 0.2 cm in length.
- *Petiolule, leaflets*.—Length: 0.1 cm. Diameter: 0.1 cm. Color: RHS 147C (Yellow-Green). Texture: Smooth. Thorns: None observed.
- *Stipules*.—Arrangement and appearance: Parallel, middle part narrowing downward, margin covered in glands with 2 auricles. Length: 0.1 cm. Width: 0.4 cm. Apex: Mucronate. Base: Truncate. Color, immature leaf: Upper surface: RHS 127B (Green). Lower surface: RHS 146B (Yellow-Green). Color, mature leaf: Upper surface: RHS 137C (Green). Lower surface: RHS 136A (Green). Texture: Upper surface: Smooth, coriaceous. Lower surface: Smooth.

Flowers and inflorescence:
- *Appearance and arrangement*.—Borne singly and in small clusters of 3 to 5 flowers.
- *Fragrance*.—Moderate, sweet, and fruity.
- *Diameter of flower*.—4.0 cm when fully open.
- *Depth or height*.—1.3 cm when fully open.
- *Lastingness of flowers on the plant*.—5 to 7 days.
- *Buds*.—Length: 1.5 cm when buds are beginning to open. Width: 1.5 cm when buds are beginning to open. Surface texture: Smooth. Shape: Pointed ovoid. Margin: Entire. Color: RHS N57D.
- *Petals*.—Quantity per flower: 50 to 60. Length: 1.6 cm. Width: 1.6 cm. Shape: Elliptic. Apex: Rounded. Base: Rounded. Margin: Entire. Color, when opening (both upper and lower surfaces): RHS N57D. Color, when fully opened (both upper and lower surfaces) RHS N57D with an RHS 13D (Yellow) color spot at the petal base. Surface texture (both upper and lower surfaces): Smooth.
- *Sepals*.—Quantity per flower: 5. Length: 1.0 cm. Width: 0.4 cm. Shape: Lanceolate. Apex: Acute. Base: Truncate. Margin: 2 are hoary and 3 are pinnatified slightly. Color, when opening: Upper surface: RHS 146C (Yellow-Green). Lower surface: RHS 138B (Green). Color, when fully open: Upper surface: RHS 146B (Yellow-Green). Lower surface: RHS 138B (Green). Surface texture: Upper surface: Glandular. Lower surface: Hoary.

Reproductive organs:
- *Stamens*.—None observed.
- *Pistils*.—Quantity per flower: 30 to 35. Pistil length: 0.4 cm. Stigma shape: Orbicular. Stigma color: RHS 156C (Greyed-White). Style length: 0.3 cm. Style color: RHS 156C (Greyed-White). Receptacle: Height: 1.0 cm. Diameter: 0.8 cm. Color: RHS 137C (Green). Texture: Smooth.

Fruit and seed set: None observed.

Disease and pest/insect resistance: Resistant to the common rose diseases of powdery mildew, rust, and black spot.

COMPARISON WITH PARENTAL LINES AND COMMERCIAL VARIETY

'ZARsunfrapk' is a distinct variety of rose and is distinguished from its parents as described in Table 1.

TABLE 1

| Comparison with Parental Lines | | | |
|---|---|---|---|
| Characteristic | 'ZARsunfrapk' | Female Parent 'MORsegold' | Male Parent KNOCK OUT 'RADrazz' |
| Plant size - 2 year old plant | 25.0 cm × 20.0 cm | 60.0 cm in height and 45.0 cm in width or spread | 1.5 m in height and 1.2 m in width or spread |
| Flower color | RHS N57D (Red-Purple) | Canary yellow | RHS 53C to RHS 53D (Red group) |

'ZARsunfrapk' is a distinct variety of rose and is distinguished from the commercial comparison variety 'JACBunch' (U.S. Plant Pat. No. 12,050) as described in Table 2.

TABLE 2

| Comparison with Commercial Line | | |
|---|---|---|
| Characteristic | 'ZARsunfrapk' | 'JACBunch' |
| Flower color | RHS N57D (Red-Purple) | RHS 47D (Red) |
| Fragrance | Moderate and fruity | Slight |
| Plant size - 2 year old plant | 25.0 cm × 20.0 cm | 75.0 cm in height and 60.0 cm in width or spread |

I claim:

1. A new and distinct variety of rose plant named 'ZARsunfrapk' as illustrated and described herein.

* * * * *